(12) United States Patent
Hirokawa et al.

(10) Patent No.: US 8,983,025 B2
(45) Date of Patent: Mar. 17, 2015

(54) X-RAY CT APPARATUS

(75) Inventors: Koichi Hirokawa, Tokyo (JP); Yoshiaki Sugaya, Tokyo (JP); Toshiyuki Irie, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1219 days.

(21) Appl. No.: 12/525,707

(22) PCT Filed: Feb. 7, 2008

(86) PCT No.: PCT/JP2008/052019
§ 371 (c)(1),
(2), (4) Date: Aug. 4, 2009

(87) PCT Pub. No.: WO2008/096813
PCT Pub. Date: Aug. 14, 2008

(65) Prior Publication Data
US 2010/0104159 A1    Apr. 29, 2010

(30) Foreign Application Priority Data

Feb. 8, 2007 (JP) ................................ 2007-029501

(51) Int. Cl.
| | |
|---|---|
| *A61B 6/00* | (2006.01) |
| *G01N 23/00* | (2006.01) |
| *G21K 1/12* | (2006.01) |
| *H05G 1/60* | (2006.01) |
| *A61B 6/03* | (2006.01) |
| *G01T 1/00* | (2006.01) |

(52) U.S. Cl.
CPC ............. *A61B 6/542* (2013.01); *A61B 6/032* (2013.01); *A61B 6/4085* (2013.01); *G01T 1/00* (2013.01)
USPC .................................. 378/15; 378/16; 378/4

(58) Field of Classification Search
None
See application file for complete search history.

(56) References Cited

U.S. PATENT DOCUMENTS

| | | | | |
|---|---|---|---|---|
| 2004/0086076 | A1* | 5/2004 | Nagaoka et al. | 378/4 |
| 2004/0109532 | A1* | 6/2004 | Ford et al. | 378/57 |
| 2005/0220265 | A1* | 10/2005 | Besson | 378/16 |
| 2006/0018435 | A1 | 1/2006 | Toth et al. | |
| 2009/0161818 | A1* | 6/2009 | Sakurai et al. | 378/15 |

FOREIGN PATENT DOCUMENTS

| | | |
|---|---|---|
| JP | 2004-73397 | 3/2004 |
| JP | 2004-105382 | 4/2004 |
| JP | 2006-26417 | 2/2006 |

OTHER PUBLICATIONS

Chan et al., "Scattered Radiation Level During Computed Tomography Fluorosocopy" J HK Coll Radiol, 2002, 5:19-23.*

* cited by examiner

*Primary Examiner* — Neal Sereboff
(74) *Attorney, Agent, or Firm* — Cooper & Dunham LLP

(57) ABSTRACT

An X-ray CT apparatus is configured capable of properly calculating a radiation dosed amount more approximating to an actually exposed radiation dose that includes scattering rays of an examined object from data measured at the scanning time.
A function or table showing a relationship between data obtained on the basis of the measured data of the object detected by an X-ray detector at the scanning time and the radiation dosed amount is stored in advance; and the X-ray CT apparatus calculates the radiation dosed amount of the object in accordance with the data obtained on the function or table showing the relationship between the data obtained on the basis of the measured data of the object stored in advance and the radiation dosed amount.

5 Claims, 15 Drawing Sheets

FIG. 1
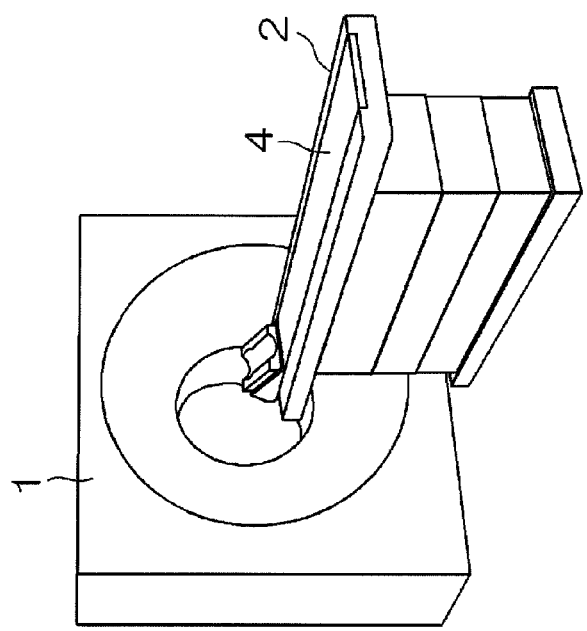
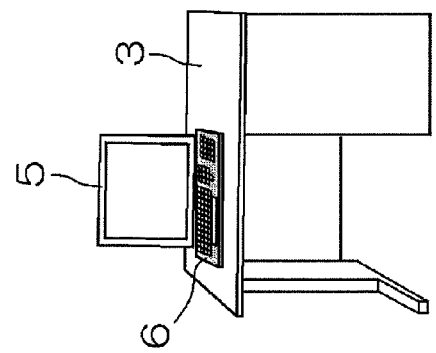

X-RAY CT APPARATUS

TECHNICAL FIELD

The present invention relates to an X-ray CT apparatus, in particular to an X-ray CT apparatus capable of measuring radiation dose of an object to be examined.

BACKGROUND ART

A multi-slice X-ray CT apparatus is for obtaining projection data of an object by irradiating cone beams, i.e. pyramidal X-ray beams from an X-ray source to the object and measuring the X-rays which have passed through the object by an X-ray detector in which detection elements are disposed in 2-dimensional direction (channel direction and row direction).

Also, a single-slice X-ray CT apparatus is for obtaining projection data of the object by irradiating fan beams, i.e. fan-shaped X-ray beams from the X-ray source to the object by measuring the X-rays which have passed through the object by an X-ray detector in which detection elements are disposed in 1 array (in channel direction).

In either case, they reconstruct tomographic images of the object by rotating, around the object, the X-ray source and the X-ray detector which are disposed opposite to each other, acquiring projection data of the object from many directions, carrying out reconstruction filtering process for deblurring, and performing back projection on the projection data of the object.

Projection data is acquired in discrete positions of the X-ray source (hereinafter referred to as "view"), and the number of views for one rotation of the X-ray source are normally several hundred to several thousand. Also, projection data for one view is composed of the data of channel number X row number (row number for the single-slice X-ray CT apparatus=1) of the X-ray detector.

The projection data acquired in a predetermined view is referred to as "projection data in the relevant view". Also, the operation for acquiring the projection data for the number of views necessary for reconstructing one piece of CT image is referred to as "scan".

The X-ray CT apparatus is an image diagnostic apparatus which has high versatility capable of diagnosing in a wide range of an entire body, and its usability has further increased due to development of multi-slice function and speeding up of scanning function. However, because X-rays are used to be applied to the object, it is still necessary to make an effort to reduce radiation dose to the object as much as possible. In order to reduce the radiation dose to the object, it is important to accurately grasp and control the radiation dose at the time of the actual scanning.

The conventional X-ray CT apparatuses have configuration that CTDI (CT Dose Index) prescribed in IEC60601-2-44 is displayed as radiation dose upon scanning on a display device of a console prior to actual scanning.

However, CTDI value to be displayed here is set assuming an acrylic phantom having 160 mm of diameter in the head region and an acrylic phantom having 320 mm of diameter in the abdominal region.

For example, acrylic equivalent diameter in an abdominal region for an average adult is 250 mm, which causes about a 30% (=320/250-1) difference compared to CTDI. If the influence of the difference thereof on radiation dose is measured, for example, in the case of scanning with 120 kV of tube voltage, the patient suffers a loss of 25% due to unreasonable under-estimation.

In other words, the radiation dose displayed on the display device of the console in accordance with the IEC standard is merely a conversion of the radiation dose measured in advance using the reference phantom which is given one kind for each of head region and abdominal region considering the scan condition for actual application, which has a gap from the radiation dose considering the actual physique of the object.

As a technique for improving such error, the X-ray CT apparatus for calculating the distribution of X-ray absorption coefficient from the CT value distribution obtained by a CT apparatus to calculate actual radiation dose to the object is proposed in Patent Document 1. By such X-ray CT apparatus, it is possible to obtain radiation dose distribution in the object and estimate the radiation dose in the respective tissues.

Patent Document 1: JP-A-2005-074000

DISCLOSURE OF THE INVENTION

Problems to be Solved

In the X-ray CT apparatus proposed in Patent Document 1, radiation dose in a slice plane is calculated based on the X-ray absorption coefficient calculated from the CT value distribution of a reconstructed image.

However, the X-ray absorption coefficient directly indicates attenuation rate of X-rays, and is not an index for calculating scattered X-rays in the body of the object. Therefore, influence of scattered X-rays is not considered in the X-ray CT apparatus proposed in Patent Document 1.

While the ratio between primary radiation and scattered X-rays differs depending on the condition of X-rays or size of the object, for example, when the tube voltage is 120 kV, the ratio between primary radiation and scattered X-rays in the central region of the acrylic phantom having 250 mm of diameter is estimated as about 2:8 wherein the larger part is occupied by the scattered X-rays. Therefore, it is significant to consider scattered X-rays in calculation of radiation dose.

The objective of the present invention is to provide an X-ray CT apparatus capable of properly calculating radiation dose which is better-approximated to actual radiation including scattered X-rays of the object using measured data of the object upon scanning, considering the above-described factors.

Means to Solve the Problem

In order to solve the above-mentioned problem, the X-ray CT apparatus of the present invention comprises:

an X-ray source configured to irradiate X-rays to an object to be examined;

an X-ray detector disposed facing the X-ray source, configured to detect the X-rays transmitted the object;

a scanner having the X-ray source and the X-ray detector, configured to rotate them around the object;

an image reconstruction device configured to reconstruct a tomographic image of the object based on the transmitted X-ray amount detected by the X-ray detector; and an image display device configured to display the tomographic image reconstructed by the image reconstruction device, characterized in further comprising:

storage means configured to store a function or a table expressing a relationship between the data obtained based on the measured data of the object detected by the X-ray detector and radiation dose; and radiation dose calculating means configured to calculate radiation dose upon scanning a tomographic image based on the data obtained using the measured data of the object detected by the X-ray detector upon scanning the tomographic image and a function or a table.

In accordance with the X-ray CT apparatus of the present invention, a function or a table expressing the relationship between the data obtained based on the measured data of the object detected by an X-ray detector and radiation dose is stored in advance, and radiation dose of the object is calculated using the data obtained based on the measured data of the object and the function or the table expressing the relationship between the data obtained based on the measured data of the object which is stored in advance and the radiation dose. Here, the relationship between the data obtained based on the measured data of the object and radiation dose is such as the relationship between projection data of the object generated by correcting the measured data of the object and radiation dose, or the relationship between the difference of measured data of the object and those without the object and radiation dose. Also, the function or the table stored in storage means is calculated from radiation dose of a circular or elliptical phantom measured using a circular or elliptical phantom.

In accordance with the above-described X-ray CT apparatus, it is possible to properly calculate actual radiation dose of the object from the data of the object measured at the time of scanning.

EFFECT OF THE INVENTION

In accordance with the present invention, it is possible to provide an X-ray CT apparatus capable of properly calculating actual radiation dose to an object from the data of the object measured at the time of scanning.

BRIEF DESCRIPTION OF THE DIAGRAMS

FIG. 1 is an external view showing the overall configuration of the X-ray CT apparatus to which the present invention is applied.

DESCRIPTION OF REFERENCE NUMERALS

1: scanner, 2: table, 3: console, 4: table top, 5: display device, 6: operation device, 7: X-ray tube controller, 8: X-ray tube, 9: collimator controller, 10: collimator, 11: X-ray detector, 12: data collecting device, 13: rotor plate, 14: rotation controller, 15: rotor plate driving device, 16: driving force transmission system, 17: object, 18: X-ray detection element, 19: tube voltage/tube current measuring device, 20: table controller, 21: table vertical movement device, 22: table-top driving device, 23: image reconstruction device, 24: storage device, 25: scan planning device, 26: table-top position sensor, 27: system controller, 28: actual radiation dose calculation device

BEST MODE FOR CARRYING OUT THE INVENTION

Best mode for carrying out the present invention will be described below based on the attached diagrams.

Figure 2:
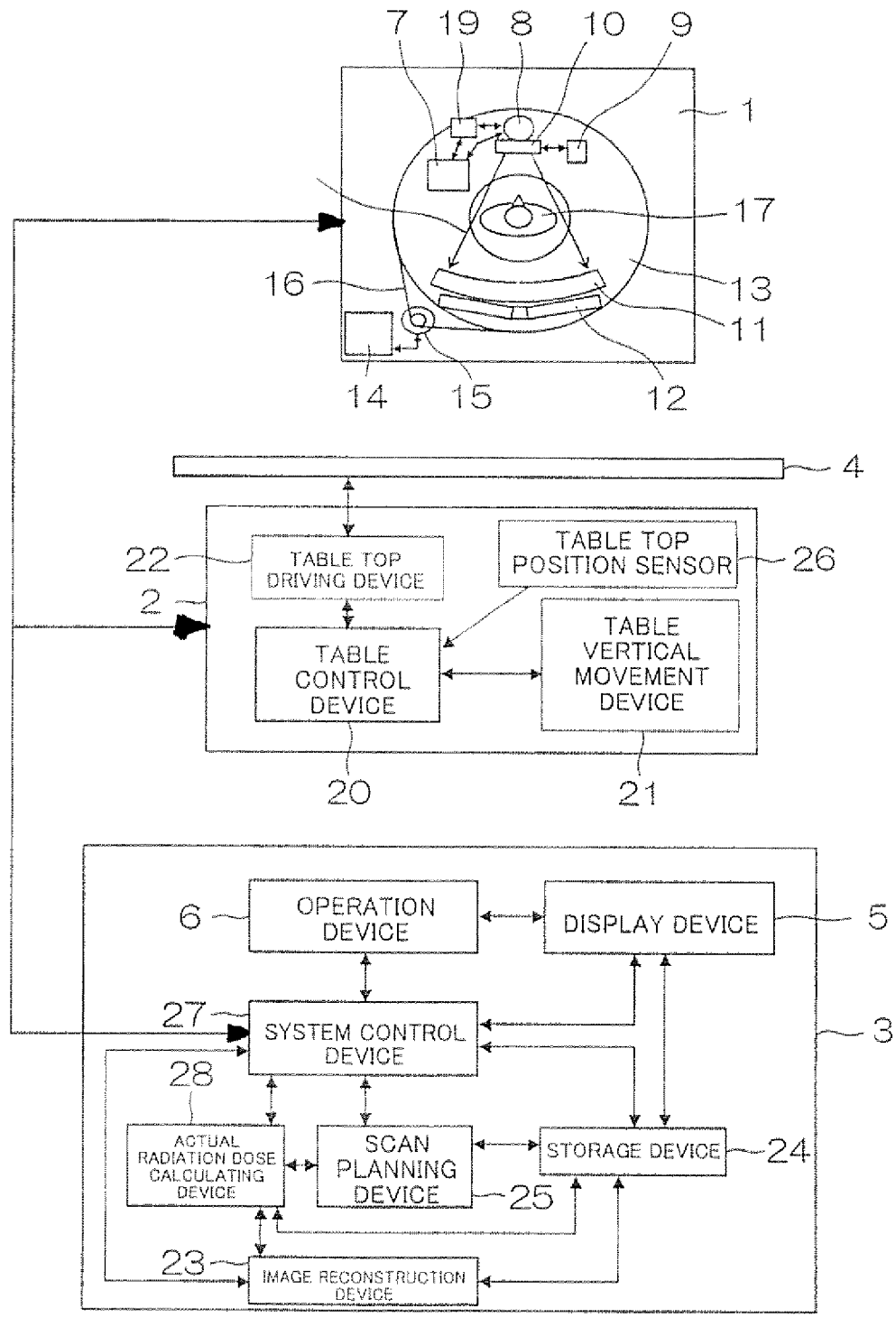
FIG. 2 is a configuration diagram showing the overall configuration of the above-mentioned X-ray CT apparatus.

FIG. 1 is an external view showing the entire configuration of the X-ray CT apparatus in the first embodiment related to the present invention, and FIG. 2 is a block configuration diagram of the above-mentioned X-ray CT apparatus.

As shown in FIG. 1, the X-ray CT apparatus mainly comprises scanner 1, patient's table 2, console 3, table top 4 provided to the patient's table 2, display device 5 and operation device 6.

As shown in FIG. 2, the scanner 1 mainly comprises X-ray tube controller 7, X-ray tube 8, collimator controller 9, collimator 10, X-ray detector 11, data collecting device 12, rotor plate 13, rotation controller 14, rotor plate driving device 15, driving force transmission system 16 and tube voltage/tube current measuring device 19.

The X-ray tube 8 is for irradiating X-rays to object 17, and the tube voltage/tube current provided to the X-ray tube 8 for irradiating X-rays are controlled by the X-ray tube controller 7. The tube voltage/tube current provided to the X-ray tube 8 are constantly measured by the tube voltage/tube current measuring device 19, and the X-ray tube controller 7 reflects the result of the measured data and controls the tube voltage/tube current provided to the X-ray tube 8 to be the previously set value.

The collimator 10 is for adjusting X-ray radiation field for irradiating the X-rays from the X-ray tube 8 as, for example, pyramidal X-ray beams i.e. cone beam X-rays to the object 17, and is controlled by the collimator controller 9.

Figure 3:
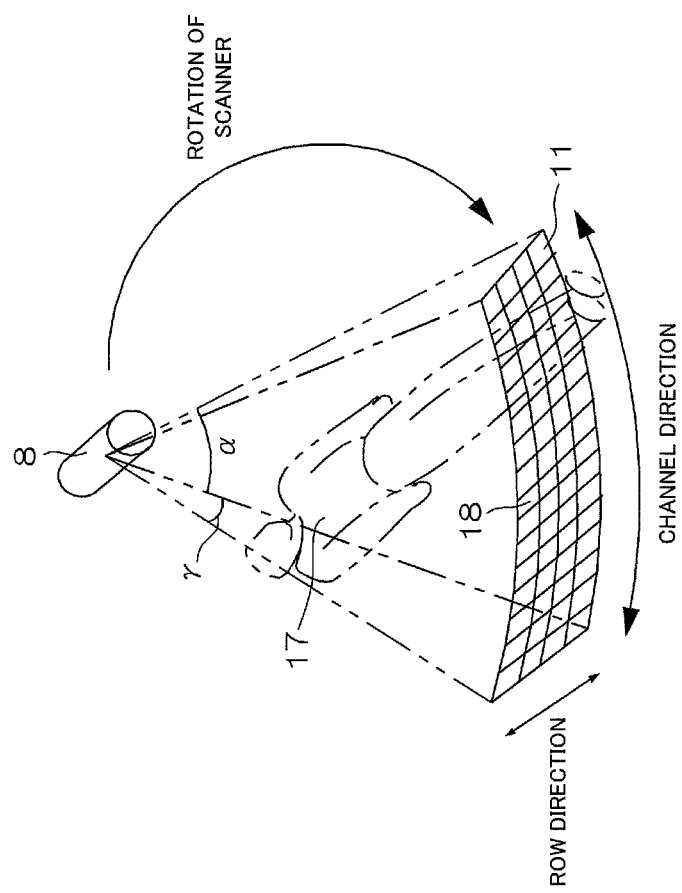
FIG. 3 is a pattern diagram for explaining the configuration of a detector of the above-mentioned X-ray CT apparatus and its relationship to X-ray irradiation.

The X-ray detector 11 comprises, as shown in FIG. 3, a plurality of X-ray detection elements 18 provided two-dimensionally in channel direction and row direction. The X-rays irradiated from the X-ray tube 8 are transmitted through the object 17 and incident to the X-ray detector 11. The configuration of the X-ray detector 11 will be described later in detail.

The data collecting device 12 is connected to the X-ray detector 11, for collecting detected data of the respective X-ray detection elements 18 of the X-ray detector 11.

On the rotor plate 13, the above-mentioned X-ray tube controller 7, X-ray tube 8, collimator controller 9, collimator 10, X-ray detector 11, data collecting device 12 and tube voltage/tube current measuring device 19 are mounted. The rotor plate 13 is rotated by the driving force transmitted from the rotor plate driving device 15 which is controlled by the rotation controller 14 via the driving force transmission system 16.

As shown in FIG. 2, the patient's table 2 mainly comprises the table top 4, table controller 20, table vertical movement device 21, table-top driving device 22 and table-top position sensor 26.

The table controller 20 controls the table vertical movement device 21 based on information from the table-top position sensor 26 so as to control the table top 4 to be set in appropriate height. Also, the table controller 20 controls the table-top driving device 22 so as to move the table top 4 backward and forward. In this manner, the object 17 can be carried in and out of X-ray irradiation space of the scanner 1.

The console 3 mainly comprises, as shown in FIG. 2, display device 5, operation device 6, image reconstruction device 23, storage device 24, scan planning device 25, system controller 27 and actual radiation dose calculating device 28.

The display device 5 is connected to the system controller 27, for displaying reconstructed images outputted from the image reconstruction device 23 or various sorts of information contained by the system controller 28.

The operation device 6 is connected to the system controller 27, for an operator to input various commands and information thereto.

The operator can operate the X-ray CT device interactively using the display device 5 and the operation device 6.

The data collected by the data collecting device 12 in the scanner is inputted to the image reconstruction device 23 under control of the system controller 27, and the image reconstruction device 23 constructs scanograms upon scanogram imaging using the scanogram projection data (object's perspective data) collected by the data collecting device 12, and reconstructs CT images upon scanning using projection data of a plurality of views collected by the data collecting device 12.

The storage device 24 is connected to the system controller 27, for storing scanograms/CT images reconstructed in the image reconstruction device 23, various data, and programs for implementing functions of the X-ray CT apparatus, etc.

The scan planning device 25 is connected to the system controller 27, for the operator to make out scan planning using the commands inputted from the operation device 6 and the scanograms read out from the storage device 24.

More specifically, when the scanograms readout from the storage device 24 are displayed on display device 5, the operator can plan CT image reconstructing position (hereinafter referred to as slice position) by specifying the coordinate of the slice position on the displayed object's scanogram using the operation device 6. Further, information of the slice position planned as above is stored in the storage device 24, and used also for the scan planning device 25 to plan X-ray control condition, etc. As for the function for planning optimal X-ray dose for the object on which scanogram imaging is performed in advance, detailed explanation will be omitted since a variety of commonly known techniques (for example, JP-A-2001-043993) can be used.

The system controller 27 is connected to the scanner 1 and the patient's table 2, and controls the X-ray tube controller 7 in the scanner 1, collimator controller 9, data collecting device 12, rotation controller 14, and the table controller 20 in the patient's table 2.

The actual radiation dose calculating device 28 is connected to the system controller 27, for calculating radiation dose of the object 17 using the measured data of the object 17 detected in the X-ray detector 11. The method for calculating radiation dose of the object 17 will be described later.

Next, the X-ray detector 11 will be described.

As shown in FIG. 3, the X-ray detector 11 is configured wherein, for example, a plurality of X-ray detection elements 18 formed by combination of scintillator and photo diode are two-dimensionally arrayed in channel direction and row direction (slice direction).

The X-ray detection elements 18 configure an X-ray incident plane curved cylindrically as a whole or in broken line with respect to the channel direction, wherein channel number "i" is, for example, in the range of 1~1000 (i.e. 1~1000 X-ray detection elements are arrayed in the channel direction) and row number "j" is, for example, in the range of 1~1000 (i.e. 1~1000 X-ray detection elements are arrayed in the row direction).

Figure 4:
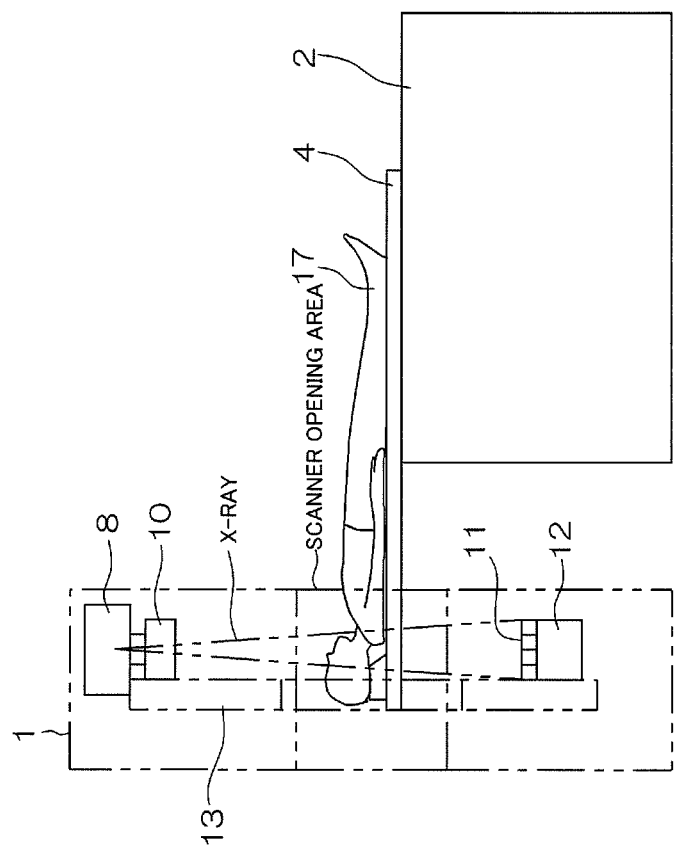
FIG. 4 is a pattern diagram showing the relationship between the scanner, the patient's table of the above-mentioned X-ray CT apparatus and the object viewed from the side.

As shown in FIG. 3 and FIG. 4, the cone beam X-rays wherein fan angle α and cone angle γ are adjusted by opening width of the collimator 10 are irradiated to the object 17 placed on the table top 4 of the patient's table 2 and carried into the opening of the scanner 1, and the X-ray detector 11 detects the X-rays transmitted through the object 17.

Figure 5:
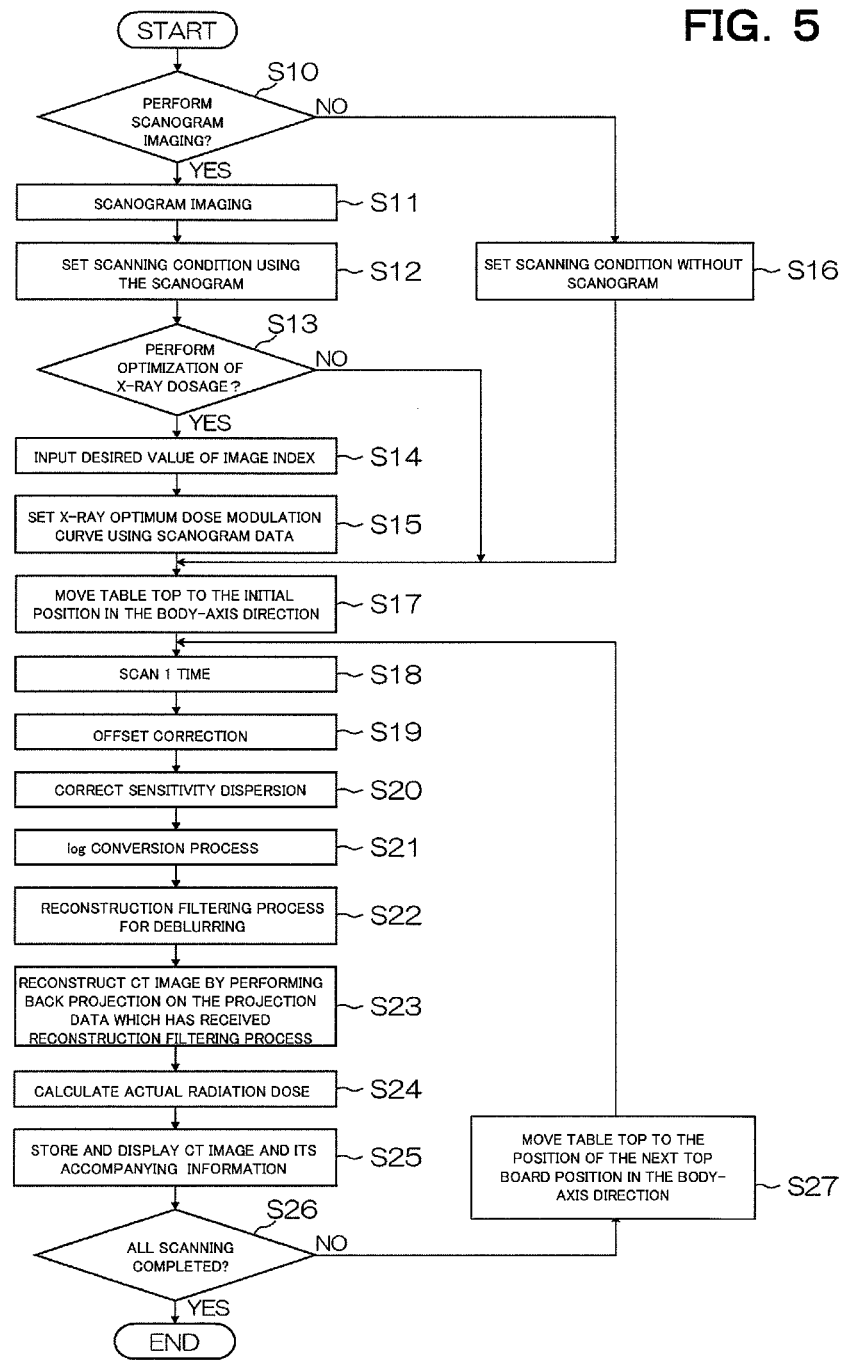
FIG. 5 is a flowchart showing the flow of the entire process of the above-mentioned X-ray CT apparatus.

Next, mechanism of the X-ray CT apparatus configured as above will be described. FIG. 5 is a flowchart showing the flow of the entire process of the X-ray CT apparatus. The process below is performed under control of the system controller 27. Though the mechanism will be described assuming non-helical scanning, the embodiment of the present invention is not intended to be limited to non-helical scanning, and is applicable also to helical scanning.

First, the operator gives a command whether or not to perform scanogram imaging to the system controller 27 using the operating device 6, and the process below is determined based on the command (step S10).

In the case that the command is given to perform scanogram imaging in step S10 ("YES" is selected in step S10), steps for setting scan condition using scanogram data (steps S11~S15) is to be carried out.

In the case that the command is given to perform scanogram imaging in step 10 ("YES" is selected in step S10), scanogram imaging of the object is carried out (step S11), and scan condition is set using the scanogram (step S12). The scan condition here means various conditions such as positions of beginning CT image/ending CT image in the body-axis direction, CT image construction intervals in the body-axis direction, X-ray tube voltage, X-ray tube current, scanning time (time necessary for 1 rotation), X-ray collimation condition, kind of reconstruction filtering function, and FOV size.

After scan condition is set, the operator determines whether optimization of X-ray dose is to be carried out or not (step S13).

In the case that implementation of X-ray dose optimization is commanded ("YES" is selected in step S13), the operator inputs desired value of image index using operation device 6 of the console 3 (step S14), and optimal X-ray dose modulation curve is calculated by the scan planning device 25 using the inputted desired value of image index and an object model wherein the scanogram data imaged in step S11 is analyzed (step S15). The calculated data of the optimal X-ray dose modulation curve is transmitted to the X-ray tube controller 7 via the system controller 27 so as to control the X-ray tube so that optimal X-ray dose is irradiated with respect to the cross-section of the object 17 upon scanning.

In the case that X-ray dose optimization is not to be performed ("NO" is selected in step S13), setting process of scan condition is ended.

In this manner, setting process of scan condition (steps S11~S15) in the case of performing scanogram imaging ("YES" is selected in step S10) is ended.

In the case that scanogram imaging is not to be performed ("NO" is selected in step S10), setting of scan condition is performed without a scanogram (step S16). While the scan condition to be set here is the same as those described in step S12, as for the positions of a beginning CT image and an ending CT image in the body-axis direction, they can be set down by the relative position between the reference position which is set in advance using a light localizer (not shown in the diagram).

After setting the scan condition, scanning is to be performed (steps S17~S27).

The table top 4 is moved to a predetermined initial position in the body-axis direction (step S17).

In a predetermined position in the body-axis direction, scanning is performed one time (step S18).

With respect to the measured data of the object obtained by scanning, in the image reconstruction device 23, offset correction (step S19) for subtracting output of data collection device when X-rays are not irradiated (offset output) from output of data collection device during measurement of an object, sensitivity dispersion correction (step S20) for correcting sensitivity dispersion of the respective detection elements, and log conversion process (step S21) for converting the measured data after correction into projection data which is proportional to X-ray absorption coefficient integration value in an X-ray transmission path are performed. The data generated by various correction/conversion process (steps S19~S21) with respect to the measured data for the purpose of generating projection data of the object is used for reconstructing CT images (steps S22~S23), and also for actual radiation dose calculating process (step S24) to be performed by the actual radiation dose calculating device 28.

Next, process for reconstructing CT images (steps S22~S23) will be described.

In the image reconstruction device 23, reconstruction filtering process for deblurring is performed with respect to projection data of the object generated in step S21 (step S22). Then a CT image in a predetermined position in the body-axis direction of the object 17 is reconstructed (step S23) by performing back projection on the projection data which is performed with reconstruction filtering process by the image reconstruction device 23.

Also, the actual radiation dose calculating device 28 calculates actual radiation dose (step S24) by analyzing the data generated by correction process (steps S19~S21) for generating projection data of the object. The method for calculating actual radiation dose will be described later in detail.

Figure 6:
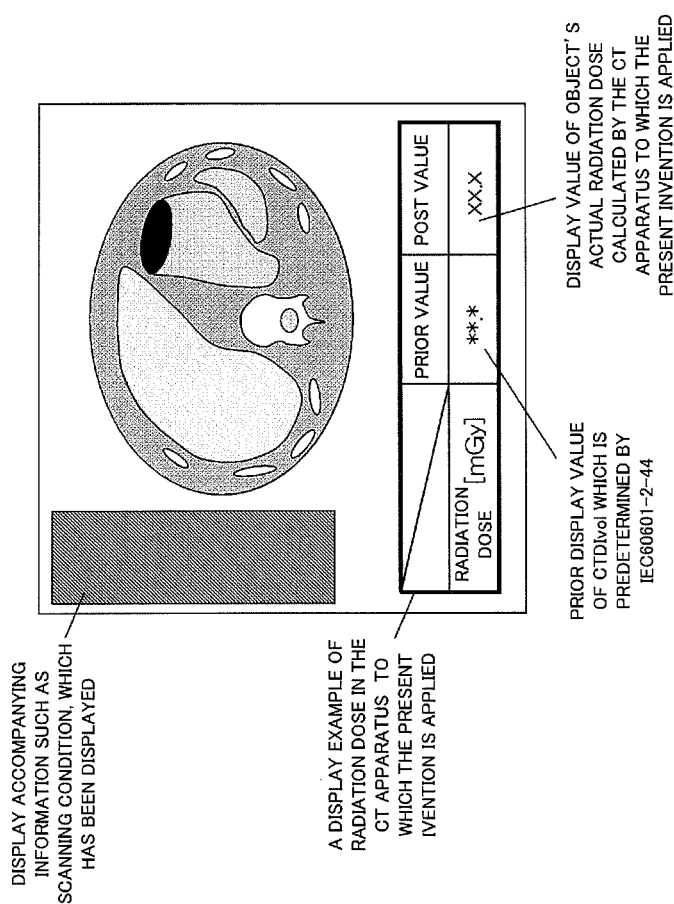
FIG. 6 is a display example wherein radiation dose is displayed on a display device of the above-mentioned X-ray CT apparatus.

The CT images reconstructed in step S23 are stored in the storage device 24 along with the actual radiation dose calculated in step S24 or collateral information such as other scan conditions, and displayed on the display device 5 (step S25). A display example on the display device 5 is shown in FIG. 6.

Here, $CTDI_{vol}$ prescribed in IEC60601-2-44 is set as a prior value and the actual radiation dose calculated by the CT apparatus to which the present invention is set as a post value, and those values are displayed so that standard expected value and actual radiation value can be clearly compared.

Next, whether the entire scanning process is completed or not is determined by the system controller 27 (step S26).

When the entire scanning process is completed ("YES" is selected in step S26), the series of processes is to be ended.

When the entire scanning process is not completed ("NO" is selected in step S26), the table top 4 is to be moved to the next table-top position in the body-axis direction (step S27). Then the scanning is to be carried out again (step S18). In this manner, scanning can be repeated as necessary.

In this manner, the series of process of the X-ray CT apparatus is ended. The method for calculating actual radiation dose (step S24) will be described below in detail.

First Embodiment for Calculating Actual Radiation Dose

In the first embodiment, the value equivalent to a cross-sectional area of the object is calculated from the projection data generated in step S21 so as to calculate actual radiation dose of the object from the relationship between the value equivalent to cross-sectional area of the object and radiation dose.

Figure 7:
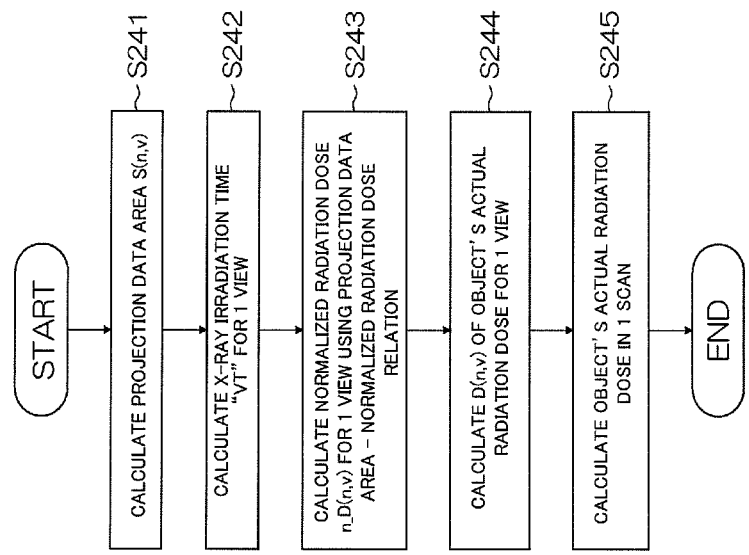
FIG. 7 is a flowchart showing the flow of process in first embodiment for calculating actual radiation dose in the above-mentioned X-ray CT apparatus.

FIG. 7 is a flowchart showing the flow of process in the first embodiment for calculating actual radiation dose using the X-ray CT apparatus. The process described below is to be carried out by the actual radiation dose calculating device 28.

Figure 8:
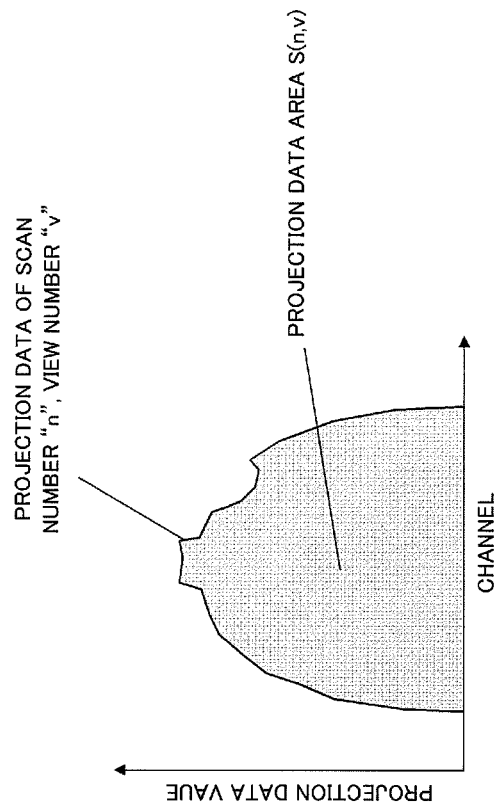
FIG. 8 shows projection data of an object for 1 view in the first embodiment for calculating actual radiation dose in the above-mentioned X-ray CT apparatus.

First, projection data area S(n,v) is calculated from the projection data generated in step S21 (step S241). FIG. 8 shows projection data of the object in scan number "n" (n: 0~N−1) and view number "v" (v: 0~V−1), and the projection data area at this time is S(n,v). The projection data area is the value equivalent to the cross-sectional area of the object.

Next, X-ray irradiation time "VT" for 1 view is calculated using formula 1 (step S242).

$$VT = XT/V \qquad \text{[Formula 1]}$$

The "XT" indicates X-ray irradiation time for 1 scan.

Then normalized radiation dose n_D(n,v) in scan number "n" and view number "v" is calculated by X-ray irradiation time "VT" for one view, S(n,v), tube current XA(n,v) which is applied to the view and tube voltage XV being set as scan condition in advance (step S243). For tube current XA(n,v), the value measured in the tube voltage/tube current measuring device 19 is to be used.

The method for calculating normalized radiation dose n_D (n,v) in step S243 will be described below.

Figure 9:
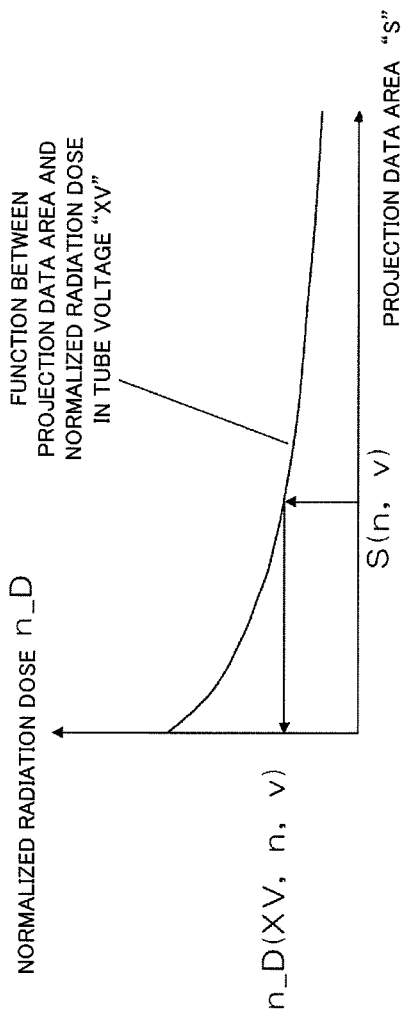
FIG. 9 shows a function between projection data area and normalized radiation dose in the first embodiment for calculating actual radiation dose in the above-mentioned X-ray CT apparatus.

For calculating normalized radiation dose n_D(n,v), the relationship between projection data area and normalized radiation dose as shown in FIG. 9 is used. The projection data area is calculated, as described above, based on projection data of the object generated by performing various correction/conversion process on the measured data of the object. In other words, the relationship between the measured data of the object and radiation dose here means the relationship between projection data area of the object and normalized radiation dose. The normalized radiation dose here means the radiation dose of the object in the case that the product of tube current and irradiation time is a certain fixed value.

Conversion function from projection data area to normalized radiation dose is set in advance and stored in the storage device 24 as described below. The stored conversion function is read out to the actual radiation dose calculating device 28 and used as need arises.

In a plurality of phantoms having different cross-sectional areas, radiation dose is measured in advance for each of the plurality of tube currents so as to calculate normalized radiation dose. Using the result of calculation, conversion function from projection data area for every tube voltage (corresponds to the value equivalent to the cross-sectional area of the object) to normalized radiation dose is calculated in a form of, for example, interval cubic polynomial to be described later. The result of calculation thereof is stored in the storage device 24.

Here, while the measured value according to CTDI of IEC60601-2-44 may be used (except that the phantom having not only two kinds of diameters but greater kinds of diameters should be used) for the radiation dose to be the basic data of conversion function from the projection data area for every tube voltage to the normalized radiation dose, it is more desirable to use the value measured by a more accurate method as described below.

Figure 10:
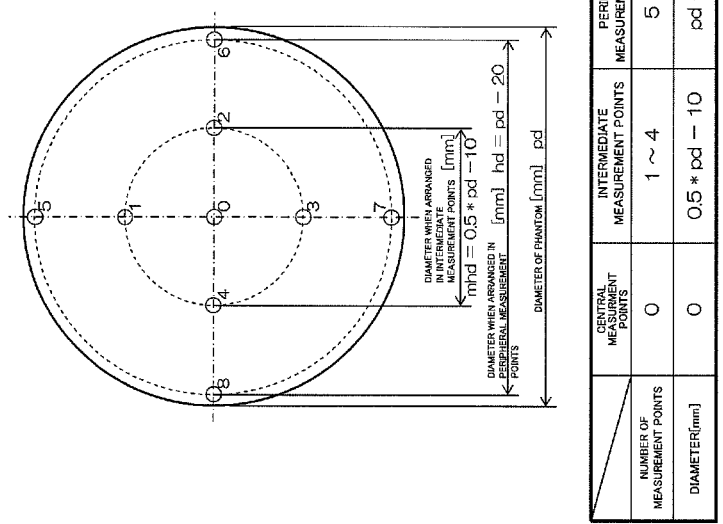
FIG. 10 shows measurement points in a cross-section of a phantom for measuring radiation dose in the first embodiment for calculating actual radiation dose in the above-mentioned X-ray CT apparatus.

As shown in FIG. 10, in 9 places on a cross-section of a phantom, radiation dose is measured according to $CTDI_{100}$ of the IEC standard at tube voltage XV, tube current XA and X-ray irradiation time XT. Using the measurement result, radiation dose D_pd(XV,XA,XT) in the phantom having diameter pd[mm] is calculated by formula 2.

$$D\_pd(XV, XA, XT) = \qquad \text{[Formula 2]}$$
$$-\frac{1}{6} * CTDI_{100\_0} + \frac{2}{9} * \sum_{q=1}^{4} CTDI_{100\_q} + \frac{5}{72} * \sum_{q=5}^{8} CTDI_{100\_q}$$

Here, $CTDI_{100\_q}$ is the radiation dose measured according to $CTDI_{100}$ in measurement point number q.

The procedure for performing actual calculation of radiation dose using conversion function from projection data area to normalized radiation dose will be described below.

In the case that tube voltage is "XV" and projection data area is S(n,v), when interval number "m" is Sm≤S(n,v)<Sm+1, normalized radiation dose n_D(XV,n,v) is calculated by formula 3 using coefficient sequence $c_{m\_0} \sim c_{m\_3}$ in the interval.

$$n\_D(XV, n, v) = \sum_{k=0}^{3} c_{m\_k} * S(n, v)^k \qquad \text{[Formula 3]}$$

After calculating normalized radiation dose n_D(XV,n,v), actual radiation dose D(n,v) in this view is calculated using formula 4 (step S244).

$$D(n,v) = n\_D(XV,n,v) * XA(n,v) * VT \qquad \text{[Formula 4]}$$

Then by obtaining the actual radiation dose for all views in scan number "n", the actual radiation dose D (n) in scan number "n" is calculated using formula 5 (step S245).

$$D(n) = \sum_{V=0}^{V-1} D(n, v) \qquad \text{[Formula 5]}$$

In accordance with the present embodiment, since projection data area is calculated as information indicating X-ray attenuation amount in the object from the object's measured data detected in the X-ray detector and radiation dose is obtained from the function or the table between projection data area and normalized radiation dose, it is possible to calculate radiation dose of the object considering physique of the object.

Also, in accordance with the present embodiment, the conversion function or the table between projection data area of the object and normalized radiation dose makes it possible to calculate radiation dose of the object based on the measurement value including influence of the scattered X-rays measured using a circular or elliptic phantom, thus it is possible to calculate radiation dose of the object considering not only primary radiation but also scattered X-rays.

While measurement of radiation dose is performed using a circular phantom in the present embodiment, the shape of the phantom's cross-section does not have to be limited to a circular shape, and may be an elliptical or other shapes.

While coefficient sequence $c_{m\_0} \sim c_{m\_3}$ is used upon calculating normalized radiation dose n_D(XV,n,v) in the present embodiment since the conversion function from projection data area to normalized radiation dose for each tube voltage is calculated in the form of interval cubic polynomial, the form of the formula does not have to be limited thereto and quadratic or less interval polynomial or quartic or more interval polynomial may be used.

Second Embodiment for Calculating Actual Radiation Dose

While actual radiation dose is calculated by first calculating the value equivalent to a cross-sectional area of the object from projection data and further calculating radiation dose to the object from the relationship between the value equivalent to the cross-sectional area and radiation dose, the method for calculation radiation dose is not intended to be limited thereto.

Second embodiment calculates actual radiation dose using a relational expression between the difference between the output upon scanning the object in measured data and the output upon only air-transmission after offset correction and normalized radiation dose. The explanation on the similar procedures as in the first embodiment will be omitted.

Figure 11:
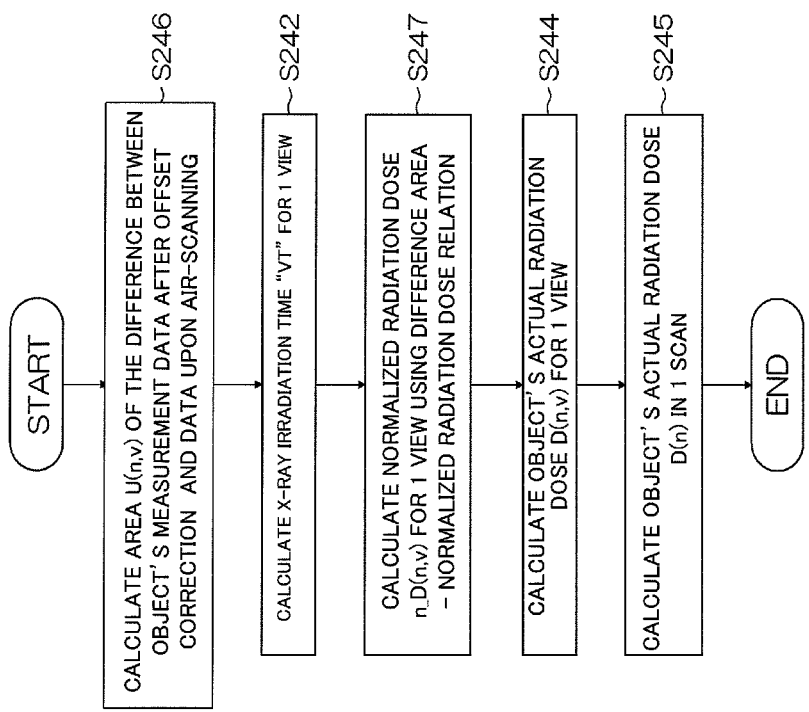
FIG. 11 is a flowchart showing the flow of process in the second embodiment for calculating actual radiation dose in the above-mentioned X-ray CT apparatus.

FIG. 11 is a flowchart showing the flow of the process in the second embodiment for calculating actual radiation dose using the X-ray CT apparatus. In the diagram, the same portions as the first embodiment will be appended with numerical references, and repeated explanation thereof will be omitted.

Figure 12:
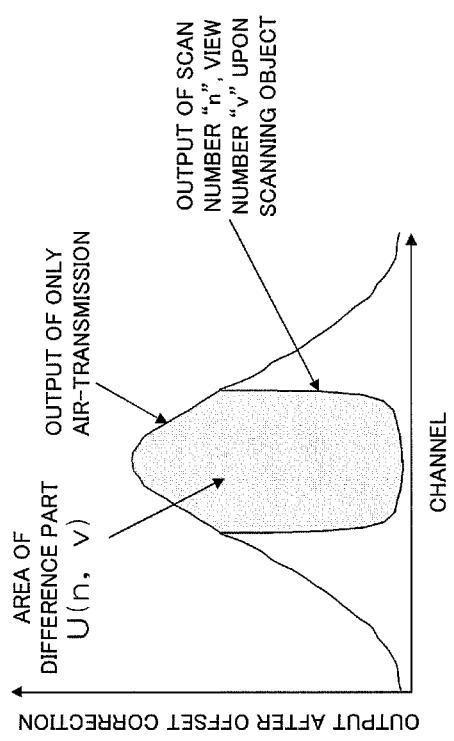
FIG. 12 shows output data after offset correction for 1 view in the second embodiment for calculating actual radiation dose in the above-mentioned X-ray CT apparatus.

Difference area U(n,v) between the data wherein the measured data of the object obtained in step S18 is performed with offset correction in step S19 and the data wherein the measured data without the object (air-scan data) is performed with offset correction is calculated (step S246). FIG. 12 is the output data after offset correction in scan number "n" (n:0~N−1) and view number "v" (v:0~V−1), and the area of difference between the output without the object (i.e. only air transmission) and the output upon measuring the object is U(n,v). The difference area U(n,v) is the value equivalent to a cross-sectional area of the object.

Next, X-ray irradiation time "VT" for 1 view is calculated (step S242).

Then normalized radiation dose n_D(n,v) in scan number "n" and view number "v" is calculated by X-ray irradiation time VT for 1 view, S(n,v), tube current XA(n,v) which is applied to the view and tube voltage XV being set in advance as scan condition (step S247).

The method for calculating normalized radiation dose n_D(n,v) in step S247 will be described below.

Figure 13:
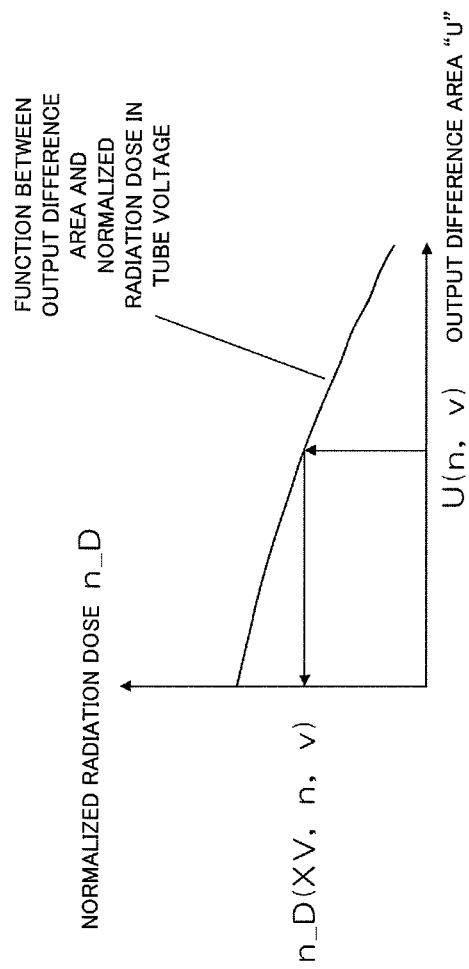
FIG. 13 shows the relationship between output difference area and normalized radiation dose in the second embodiment for calculating actual radiation dose in the above-mentioned X-ray CT apparatus.

For calculating normalized radiation dose n_D(n,v), conversion function between output difference area and normalized radiation dose as shown in FIG. 13 is used. As previously mentioned, output difference area is calculated by calculating the difference between the data wherein the measured data of the object performed with offset correction and the data wherein the measured data without the object is performed with offset correction. In other words, the relationship between the measured data of the object and radiation dose here means the relationship between output difference area and normalized radiation dose.

A function between output difference area and normalized radiation dose is obtained by first calculating normalized radiation dose by measuring radiation dose in a plurality of phantoms having different cross-sectional areas in the same manner as the first embodiment and obtaining function of radiation dose between output difference area for each tube voltage (corresponds to the value equivalent to the cross-sectional area of the object) and normalized radiation dose in the form of interval cubic polynomial, which is to be stored in the storage device 24 and read out to the actual radiation dose calculating device 28 as need arises.

The procedure for calculating radiation dose using conversion function from output difference area to normalized radiation dose will be described below.

In the case that tube voltage is "XV" and output difference area is U(n,v) when interval number "m" is $Um \leq U(n,v) < Um+1$ as shown in FIG. 13, normalized radiation dose n_D(XV,n,v) is calculated by formula 6 using coefficient sequence $g_{m\_0} \sim g_{m\_3}$ in this interval.

$$n\_D(XV, n, v) = \sum_{k=0}^{3} g_{m\_k} * U(n, v)^k \quad \text{[Formula 6]}$$

After normalized radiation dose n_D(XV,n,v) is calculated, actual radiation dose D(n,v) in this view is calculated using formula 4 (step S244). Then by obtaining actual radiation dose for all views in scan number "n", actual radiation dose D(n) in scan number "n" is calculated using formula 5 (step S245).

In accordance with the present embodiment, since the difference between the measured data of the object and those without the object (air transmission only) is calculated as information indicating X-ray attenuation amount in the object and radiation dose is obtained based on the calculated information, it is possible to calculate radiation dose of the object considering physique of the object.

Also, in accordance with the present embodiment, since calculation of radiation dose is based on the difference between measured data of the object and those without the object and measured value of radiation dose including influence of scattered X-rays using a circular or elliptic phantom, it is possible to calculate radiation dose of the object considering not only primary radiation but also scattered X-rays.

Also, in accordance with the present embodiment, since data after offset correction is used, it is possible to calculate actual radiation dose from the data preceding the generation of projection data. In other words, since more time can be taken for calculating radiation dose than the first embodiment, it is possible to calculate radiation dose even if arithmetic capacity of radiation dose calculating device 28 is lower than the one in the first embodiment.

While coefficient sequence $g_{m\_0} \sim g_{m\_3}$ is used upon calculating normalized radiation dose n_D(XV,n,v) in the present embodiment since the conversion function from output difference area to normalized radiation dose is calculated in the form of interval cubic polynomial, the form of the formula does not have to be limited thereto and quadratic or less interval polynomial or quartic or more interval polynomial may be used.

Third Embodiment for Calculating Radiation Dose

While the second embodiment calculated radiation dose of the object using relational expression between difference of the output data upon scanning the object and the output of only air-transmission after off set correction and normalized radiation dose, the method for calculating radiation dose to the object is not limited thereto.

In third embodiment, radiation dose to the object is calculated using the relational expression between the difference between the output of scan data and the output of only air transmission after offset correction and the product of normalized radiation dose, area of the object and relative absorption coefficient.

Figure 14:
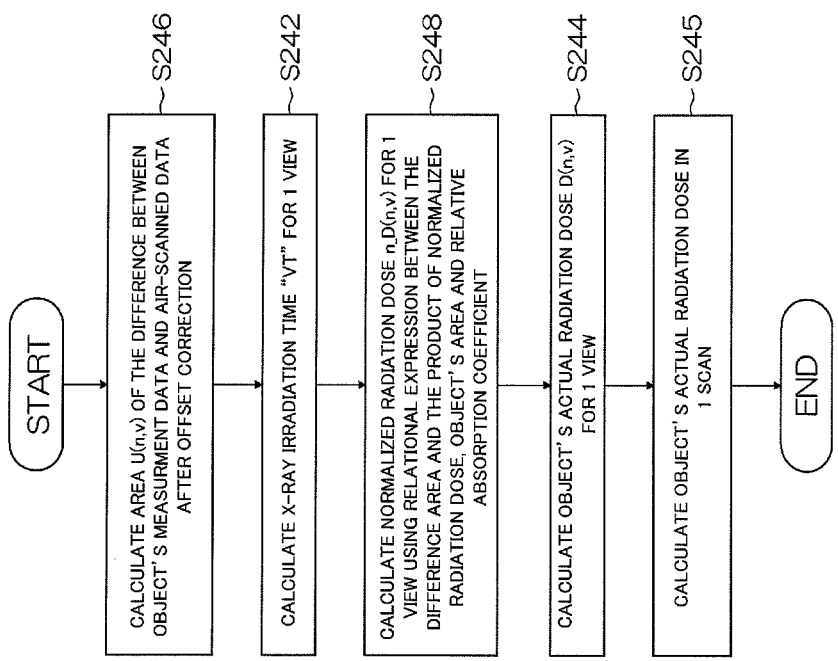
FIG. 14 is a flowchart showing the flow of process in the third embodiment for calculating actual radiation dose in the above-mentioned X-ray CT apparatus.

FIG. 14 is a flowchart showing the flow of process in the third embodiment for calculating actual radiation dose using the X-ray CT apparatus. The process described below is to be performed by the actual radiation dose calculating device 28. In the diagram, the same portions as the first and second embodiments are appended with numerical references and repeated explanation thereof will be omitted.

First, difference area U(n,v) between the data wherein measured data of the object obtained in step S18 is performed with offset correction in step S19 and the measured data without the object (air scan data) which is performed with offset correction is calculated (step S246).

Next, X-ray irradiation time VT for 1 view is calculated (step S242).

Then normalized radiation dose n_D(n,v) in scan number "n" and view number "v" is calculated by X-ray irradiation time VT for 1 view, S(n,v), tube current XA(n,v) which is applied to the view and tube voltage XV being set in advance as a scan condition (step S248).

Hereinafter, the method for calculating normalized radiation dose n_D(n,v) in step S248 will be described below.

Figure 15:
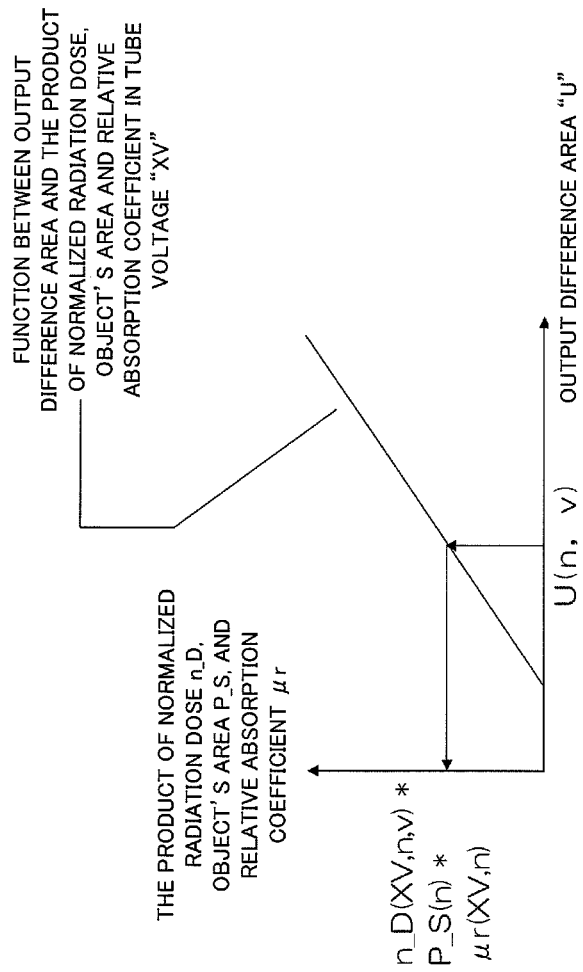
FIG. 15 shows a function curve between output difference area and the product of normalized radiation dose, area of an object and relative absorption coefficient in the third embodiment for calculating actual radiation dose in the above-mentioned X-ray CT apparatus.

Upon calculation of normalized radiation dose n_D(n,v), as shown in FIG. 15, conversion function from output difference area to the product of normalized radiation dose, area of the object and relative absorption coefficient is used. Area of the object P_S(n) in scan number "n" can be calculated from a CT image. Also, relative absorption coefficient μr(XV,n) of the object's cross-section in scan number "n" can be calculated from average CT value of the object's cross-section in a CT image using formula 7.

μr(XV,n)=(Average CT value of a cross-section of an object+1000)/1000    [Formula 7]

When the product of normalized radiation dose, area of the object and relative absorption coefficient is expressed by ψ, the function of output difference area and ψ shown in FIG. 15 can be described as formula 8 which is a linear function.

$$\varphi(XV, n, v) = \begin{cases} a*(U(n,v) - b) & (U(n,v) > b) \\ 0 & (U(n,v) \leq b) \end{cases} \quad \text{[Formula 8]}$$

Normalized radiation dose is calculated by measuring radiation dose in the same manner as the embodiment 2, the function between output difference area and ψ is obtained for every tube voltage in the form of formula 8 and stored in the storage device 24 to be read out to the actual radiation dose calculating device 28 as need arises.

Then based on the result of the above calculation, normalized radiation dose n_D(XV,n,v) is calculated using formula 9.

$$n\_D(XV,n,v)=\phi(XV,n,v)/(P\_S(n)*\mu r(XV,n))  \quad \text{[Formula 9]}$$

After normalized radiation dose n_D(XV,n,v) is calculated, actual radiation dose D(n,v) in this view is calculated using formula 4 (step S244). Then by obtaining actual radiation dose in all views in scan number "n", actual radiation dose D(n) in scan number "n" is calculated using formula 5 (step S245).

In accordance with the present embodiment, since conversion function from output difference area of the object to the product of the normalized radiation dose, the object's area and relative absorption coefficient is simple as shown in formula 8, the less coefficient is required to be stored in advance. Therefore, less process is required for determining conditions of the domain of function upon actual calculation, which saves the time for calculation.

As described above, in accordance with the X-ray CT apparatus of the present invention, it is possible to calculate and appropriately grasp radiation dose considering conditions such as physique of the object, object's position in actual scanning and scan condition, without the need of prior scanogram imaging.

The invention claimed is:

1. An X-ray CT apparatus comprising:
an X-ray source configured to irradiate X-rays to an object to be examined;
an X-ray detector disposed facing the X-ray source, and configured to detect the X-rays transmitted through the object;
a scanner in which the X-ray source and the X-ray detector are mounted, configured to rotate them around the object, for a plurality of views;
an image reconstruction device configured to reconstruct a tomographic image of the object based on a dose of the transmitted X-rays detected by the X-ray detector;
image display device configured to display the tomographic image reconstructed by the image reconstruction device;
a storage device that stores a mathematical function, or a table, representing a relationship between (a) a first value equivalent to cross-sectional area of a phantom calculated based on measured data of the phantom detected by the X-ray detector and (b) a second value corresponding to radiation dose absorbed in the phantom including scattered X-rays; and
a radiation dose calculating device configured
to calculate radiation dose absorbed in the object in a view, by inputting to the mathematical function a value equivalent to cross-sectional area of the object calculated based on measured data of the object detected by the X-ray detector upon tomographic image scanning, or by comparing the value equivalent to the cross-sectional area of the object with first values in the table, and
to calculate actual radiation dose absorbed in the object upon tomographic image scanning by using summation of the radiation dose calculated or determined for each view amongst the plurality of views.

2. The X-ray CT apparatus according to claim 1, wherein the function or the table expresses the relationship between projection data obtained by correcting measured data of the phantom and radiation dose including scattered X-rays.

3. The X-ray CT apparatus according to claim 1, wherein the function or the table expresses the relationship between difference data of measured data of the phantom and those without the phantom and radiation dose including scattered X-rays.

4. The X-ray CT apparatus according to claim 1, wherein the function or the table is created in advance based on the data obtained by measuring a plurality of phantoms having different sizes according to IEC standard.

5. The X-ray CT apparatus according to claim 1, wherein the display device displays the radiation dose calculated by the radiation dose calculating device and the radiation dose prescribed by a predetermined standard along with the tomographic image.

* * * * *